United States Patent
Hassan et al.

(10) Patent No.: US 10,599,987 B2
(45) Date of Patent: Mar. 24, 2020

(54) APPARATUSES, SYSTEMS, AND METHODOLOGIES FOR PERMEABILITY PREDICTION

(71) Applicant: KING FAHD UNIVERSITY OF PETROLEUM AND MINERALS, Dhahran (SA)

(72) Inventors: Md Rafiul Hassan, Dhahran (SA); Muhammad Imtiaz Hossain, Dhahran (SA); Abdulazeez Abdulraheem, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 744 days.

(21) Appl. No.: 15/210,301

(22) Filed: Jul. 14, 2016

(65) Prior Publication Data

US 2018/0018561 A1    Jan. 18, 2018

(51) Int. Cl.
*G06N 7/00* (2006.01)
*G06N 3/08* (2006.01)
(Continued)

(52) U.S. Cl.
CPC ............ *G06N 7/005* (2013.01); *E21B 49/00* (2013.01); *G01N 15/08* (2013.01); *G01N 33/246* (2013.01); *G06N 3/086* (2013.01)

(58) Field of Classification Search
CPC ........ G06N 7/005; G06N 3/086; E21B 49/00; G01N 15/08; G01N 33/246
See application file for complete search history.

(56) References Cited

U.S. PATENT DOCUMENTS

2015/0039235 A1   2/2015   Wiener et al.

FOREIGN PATENT DOCUMENTS

| WO | 2015/049934 A1 | 4/2015 |
| WO | 2015/152880 A1 | 10/2015 |

OTHER PUBLICATIONS

Chang et al. ("Optimization the Initial Weights of Artificial Neural Networks via Genetic Algorithm Applied to Hip Bone Fracture Prediction", Hindawi Publishing Corporation, Advances in Fuzzy Systems, vol. 2012, Article ID 951247, Jan. 23, 2012, pp. 1-9) (Year: 2012).*

(Continued)

*Primary Examiner* — Robert A Cassity
*Assistant Examiner* — Robert Lewis Kulp
(74) *Attorney, Agent, or Firm* — Oblon, McClelland, Maier & Neustadt, L.L.P.

(57) ABSTRACT

Systems, methods, and apparatuses are provided for permeability prediction. The method acquires data associated with one or more geological formations, calculates, using processing circuitry and a trained Hidden Markov model, log-likelihood values to group the data into a plurality of clusters, and trains an artificial neural network for each of the plurality of clusters when the mode of operation is training mode. Further, the method acquires one or more formation properties corresponding to a geological formation, determines using the trained Hidden Markov model, a log-likelihood score associated with the one or more formation properties, identifies a cluster associated with the one or more formation properties as a function of the log-likelihood score, and predicts a permeability based at least in part on the one or more formation properties and a trained artificial neural network associated with the identified cluster when the mode of operation is forecasting mode.

8 Claims, 9 Drawing Sheets

(51) Int. Cl.
  *G01N 15/08* (2006.01)
  *E21B 49/00* (2006.01)
  *G01N 33/24* (2006.01)

(56) References Cited

OTHER PUBLICATIONS

Huang et al. ("Spatial hidden Markov chain models for estimation of petroleum reservoir categorical variables", J Petrol Explor Prod Technol, published online May 9, 2016, pp. 1-12) (Year: 2016).*

Ja'fari et al. ("Integration of ANFIS, NN and GA to determine core porosity and permeability from conventional well log data", J. Geophys Eng 9 (2012), pp. 473-481) (Year: 2012).*

Kaydani et al. ("Permeability prediction based on reservoir zonation by a hybrid neural genetic algorithm in one of the Iranian heterogeneous oil reservoirs", Journal of Petroleum Science and Engineering 78, 2011, pp. 497-504) (Year: 2011).*

Padron et al. ("A Hidden Markov Model Approach for Lithology Identification from Logs", 3rd Conference on Artificial Applications to the Environmental Science, p. 1.1, Feb. 11, 2003, pp. 1-7) (Year: 2003).*

Baghaee et al ("A Hybrid Symbiotic Evolution-Neuro Fuzzy Strategy for Permeability Estimation of the Reservoir", Petroleum Science and Technology, 31, 2013, pp. 1135-1144) (Year: 2013).*

Pu et al ("A Pruned Cooperative Co-Evolutionary Genetic Neural Network and Its Application on Stock Market Forecast", The 26th Chinese Control and Decision Conference, Changsha, 2014, pp. 2344-2349) (Year: 2014).*

Hamada et al. ("Neural network prediction of porosity and permeability of heterogeneous gas sand reservoirs using NMR and conventional logs", NAFTA 61(10), 2010, pp. 451-460) (Year: 2010).*

Randy Haupt ("Optimum Population Size and Mutation Rate for a Simple Real Genetic Algorithm that Optimizes Array Factors", IEEE Antennas and Propagation Society International Symposium. Transmitting Waves of Progress to the Next Millennium, 2000 Digest, Salt Lake City, UT, 2000, pp. 1034-1037) (Year: 2000).*

Tarek Helmy, et al., "Hybrid computational models for the characterization of oil and gas reservoirs", Expert Systems With Applications, vol. 37, (2010) pp. 5353-5363.

Fatal A. Anifowose, et al., "Prediction of Petroleum Reservoir Properties using Different Versions of Adaptive Neuro-Fuzzy Inference System Hybrid Models", International Journal of Computer Information Systems and Industrial Management Applications, vol. 5, (2013) pp. 413-426.

Soumi Chaki, "Reservoir Characaterization: A Machine Learning Approach", Department of Electrical Engineering Indian Institute of Technology, Kharagpur, (2015), 98 pages.

* cited by examiner

APPARATUSES, SYSTEMS, AND METHODOLOGIES FOR PERMEABILITY PREDICTION

BACKGROUND

Permeability is a fundamental rock property that illustrates the ability of a fluid to flow through a given geological formation. Permeability of gas or liquid in a reservoir is a crucial factor to forecast the amount of oil or gas that resides in the reservoir and/or can be produced from the reservoir.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention. The foregoing paragraphs have been provided by way of general introduction, and are not intended to limit the scope of the following claims. The described embodiments, together with further advantages, will be best understood by reference to the following detailed description taken in conjunction with the accompanying drawings.

SUMMARY

The present disclosure relates to a method that acquires data associated with one or more geological formations, calculates, using processing circuitry and a trained Hidden Markov model, log-likelihood values to group the data into a plurality of clusters, and trains an artificial neural network for each of the plurality of clusters when the mode of operation is training mode. Further, the method acquires one or more formation properties corresponding to a geological formation, determines using the trained Hidden Markov model, a log-likelihood score associated with the one or more formation properties, identifies a cluster associated with the one or more formation properties as a function of the log-likelihood score, and predicts a permeability based at least in part on the one or more formation properties and a trained artificial neural network associated with the identified cluster when the mode of operation is forecasting mode.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1:
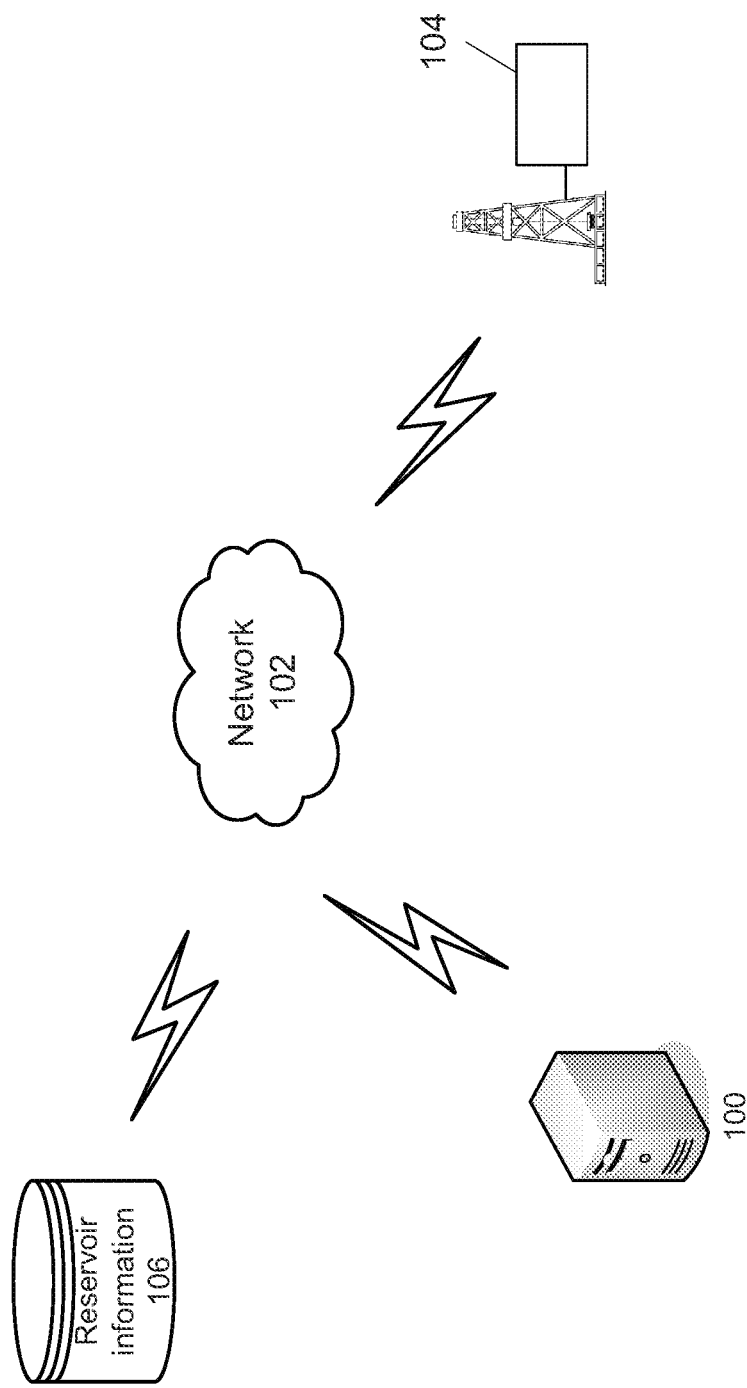
FIG. 1 is a schematic diagram of a system for permeability prediction according to one example.

Referring now to the drawings, wherein like reference numerals designate identical or corresponding parts throughout several views, the following description relates to systems, apparatus, and associated methodologies for permeability prediction.

Permeability is a fundamental rock property that illustrates the ability of gas or liquid to flow through a rock's pore space. Permeability of gas or liquid in reservoirs is a crucial factor to forecast the amount of oil or gas that resides in the reservoirs, the flow rate of oil or gas, the amount that can be recovered, the prediction of future production, and the design of production facilities as described in J. S. Lim and J. Kim, "Reservoir porosity and permeability estimation from well logs using fuzzy logic and neural networks", The Society of Petroleum Engineering (SPE), Asia Pacific Oil and Gas Conference and Exhibition, Perth, Australia, (2004). The accuracy of permeability prediction has a high significance on the productivity of petroleum production as described in B. Balan, S. Mohaghegh, and S. Ameri, "State-of-the-Art in permeability determination from well log data: part I—A comparative study, model development", SPE Eastern Regional Conference and Exhibition, West Virginia, (1995), pp. 17-21, B. Balan, S. Mohaghegh, and S. Ameri, "State-Of-The-Art in Permeability Determination From Well Log Data: Part 2—Verifiable, Accurate Permeability Predictions, the Touchstone of All Models", SPE Eastern Regional Conference and Exhibition, West Virginia, USA, (1995), pp. 104-109, M. Ali and A. Chawathe', "Using artificial intelligence to predict permeability from petrographic data", Computers & Geosciences, 26(8) (2000), pp. 915-925, and J. Lim, "Reservoir properties determination using fuzzy logic and neural networks from well data in offshore Korea", Journal of Petroleum Science and Engineering, 49(3) (2005), pp. 182-192.

Permeability may be predicted using Artificial Neural Network (ANN) as described in P. Tahmasebi and A. Hezarkhani, "A fast and independent architecture of artificial neural network for permeability prediction", Journal of Petroleum Science and Engineering, (86-87) (2012), pp. 118-126. Permeability may be predicted using ensemble of ANNs as described in S. Karimpouli, N. Fathianpour, J. Roohi, "A new approach to improve neural networks' algorithm in permeability prediction of petroleum reservoirs using supervised committee machine neural network (SC-MNN)", Journal of Petroleum Science and Engineering, 73 (3) (2010), pp. 227-232, T. Helmy, S. M. Rahman, M. I. Hossain, and A. Abdulraheem, "Non-linear heterogeneous ensemble model for permeability prediction of oil reservoirs", Arabian Journal for Science and Engineering, 38(6) (2013), pp. 1379-1395, and P. Bagheripour, "Committee neural network model for rock permeability prediction", Journal of Applied Geophysics, 104 (2014), pp. 142-148.

Permeability may be predicted using a hybrid of Genetic Algorithm (GA) based on ANN as described in M. Saemi, M. Ahmadi, and A. Varjani, "Design of neural networks using genetic algorithm for the permeability estimation of the reservoir", Journal of Petroleum Science and Engineering, 59(1) (2007), pp. 97-105, and R. Irani and R. Nasimi, "Evolving neural network using real coded genetic algorithm for permeability estimation of the reservoir", Expert Systems with Applications, 38(8) (2011), pp. 9862-9866.

However, achieving accurate prediction of permeability is still a challenge. In the system and associated methodology described herein, a Hidden Markov Model (HMM) is applied to identify and group similar input data patterns together. For each HMM based grouped data an individual co-evolutionary ANN is trained to achieve accurate prediction of permeability.

The method described herein is based on a hybrid of HMM with Co-evolutionary ANN model (HMM-COEA-ANN) technique. HMM is applied to identify and group similar input data patterns together. The system and associated methodology described herein predict permeability of a reservoir (e.g., oil reservoir, gas reservoir) with high accuracy in both Root Mean Square Error (RMSE) and Correlation Coefficient (CC). The methodology described herein is validated using datasets collected from Middle Eastern reservoirs and achieved prediction error RMSE of 0.43 with satisfactory CC of 0.93 in comparison with other models.

Figure 7:
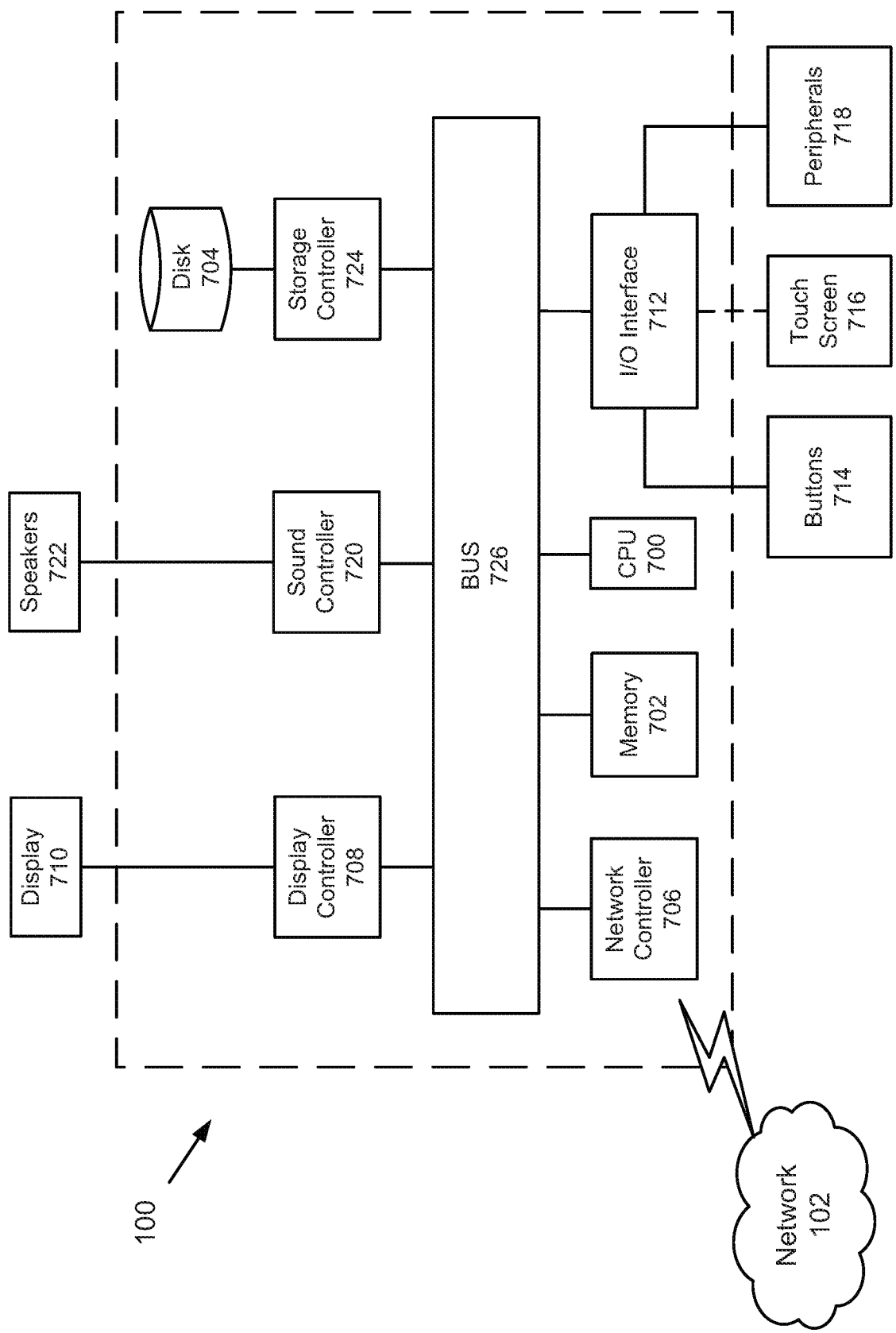
FIG. 7 is an exemplary block diagram of a server according to one example.

FIG. 1 is a schematic diagram of a system for permeability prediction according to one example. The system may include a server 100, a network 102, a permeability prediction apparatus 104, and a reservoir information database 106. The permeability prediction apparatus 104 is connected to the network 102 which is also connected to the server 100. The server 100 may manage the reservoir information database 106. The reservoir information database 106 contains data aggregated from one or more permeability prediction apparatus associated with one or more reservoirs. The server 100 may include a CPU 700 and a memory 702 as shown in FIG. 7.

The system may be used during multiple phases of the reservoir operation. The phases can include an exploration phase, a drilling phase, a completions phase, a production phase, a processing phase, and a pipeline phase. For example, during the operation phase, the output from the system may be used to forecast the productivity of the reservoir (e.g., oil well, a shale gas rig).

The server 100 may receive reservoir data of a hydrocarbon reservoir to be processed from the permeability prediction apparatus 104. Additionally and/or alternatively, the permeability prediction apparatus 104 may process the reservoir data to determine the permeability. Then, the permeability prediction apparatus 104 may upload the predicted permeability to the server 100 for further processing such as to determine an estimate of the future productivity.

In one example, the permeability prediction apparatus 104 may be used in a drilling platform. The drilling platform may be equipped with a derrick that supports a hoist for raising and lowering a drill string. Logging instruments may be positioned on the drill string to collect measurements of formation properties and drilling parameters during the drilling process. The permeability prediction apparatus 104 may include communication circuitry such as a telemetry module to communicate with the logging instruments. A logging tool may be attached at the end of a wireline that is inserted into a borehole. Sensors are used to record petrophysical properties.

Data from logging may include formation and petrophysical properties such as micro-spherically focused log (MSFL), deep resistivity (RT), porosity log (PHIT), density log (RHOB), water saturation (SWT), neutron porosity log (NPHI), caliper log (CALI), computed tomography (CT), density correction log (DRHO), and gamma ray (GR). The system may determine the permeability as a function of one or more of the formation and petrophysical properties.

The sensors may include Logging While Drilling (LWD) sensors to acquire data in real time. The logging tools may include induction tools to measure deep resistivity. The induction tools use coils and magnetic fields to develop currents in the formation whose intensity is proportional to the conductivity of the formation. The intensity of the currents is measured on receiver coils in the tool. The resistivity may also be measured by laterolog tools. The laterolog tools use electrodes to inject a current on the formation and to measures voltages at different points in the tool.

The logging tools may include an azimuthal lithodensity (ALD™) sensor to measure the density, a dual gamma ray (DGR™) sensor to measure gamma ray, a compensated thermal neutron sensor (CTN™) from HALLIBURTON to obtain the neutron porosity log. In one example, the logging tool may be a NeoScope™ LWD from SCHLUMBERGER that measure a plurality of petrophysical properties (e.g., gamma ray, borehole shape, formation sigma, density, water saturation).

The network 102 may include the Internet or any other network capable of communicating data between devices. Suitable networks can include or interface with any one or more of a local intranet, a PAN (Personal Area Network), a LAN (Local Area Network), a WAN (Wide Area Network), a MAN (Metropolitan Area Network), a VPN (Virtual Private Network), or a SAN (storage area network). Furthermore, communications may also include links to any of a variety of wireless networks, including WAP (Wireless Application Protocol), GPRS (General Packet Radio Service), GSM (Global system for Mobile Communication), CDMA (Code Division Multiple Access), TDMA (Time Division Multiple Access), cellular phone networks, GPS (Global Positioning System), CDPD (Cellular digit packet data), Bluetooth radio, or an IEEE 802.11 based radio frequency.

Figure 2:
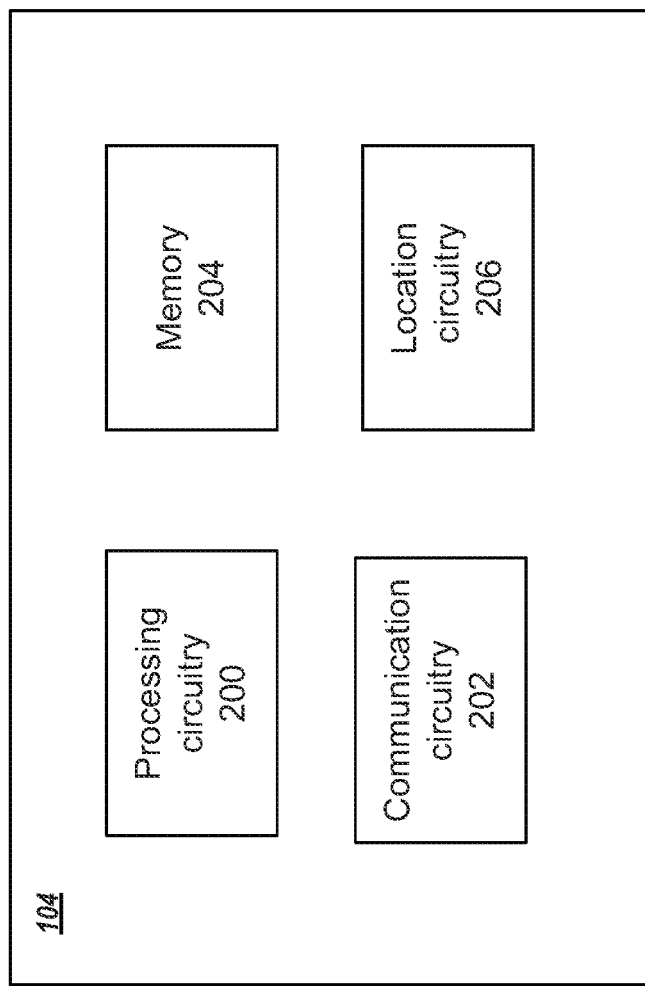
FIG. 2 is an exemplary block diagram of a permeability prediction apparatus according to one example.

FIG. 2 is an exemplary block diagram of the permeability prediction apparatus 104 according to one example. The permeability prediction apparatus 104 may include processing circuitry 200, communication circuitry 202, a memory 204, and location circuitry 206. The permeability prediction apparatus 104 may receive readings from one or more sensors (e.g., logging instruments) that may include, but are not limited to, micro-spherically focused log, deep resistivity, porosity log, density log, water saturation, Neutron porosity log, caliper log, computed tomography, density correction log, and gamma ray. In one example, the permeability prediction apparatus 104, using the processing circuitry 200, may calculate the predicted (estimated) permeability. Then, the permeability prediction apparatus 104 may upload the predicted permeability to the server 100 via the communication circuitry 202. The predicted permeability is associated with the location of the permeability prediction apparatus 104 determined via the location circuitry 206 using any localization technique as would be understood by one of ordinary skill in the art.

Figure 3:
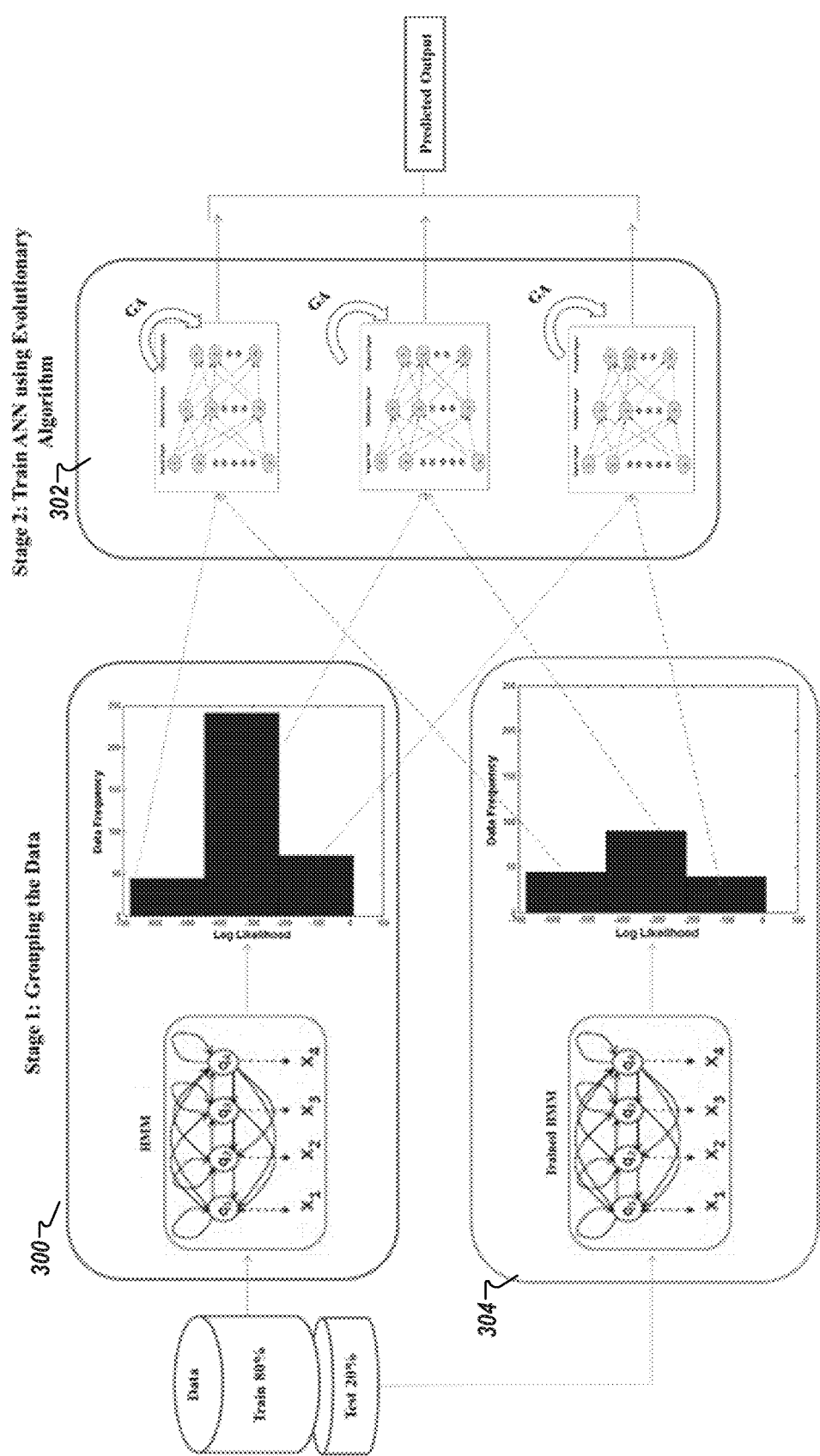
FIG. 3 is a schematic that shows stages of a method for permeability prediction according to one example.

FIG. 3 is a schematic that shows stages of the method described herein for permeability prediction according to one example. The methodology described herein includes a plurality of steps that may be divided into three stages. In a first stage 300, training data instances are grouped based on their respective HMM log-likelihood values using a trained HMM. In a second stage 302, for each of the grouped data an ANN is trained using evolutionary algorithm (EA). In a third stage 304, for a new data instance the corresponding HMM log-likelihood score is calculated using the trained HMM and then the group wherein the new data instance belong is identified. The ANN for the identified group is used to predict the permeability given the new data instance.

In stage one 300, training data are grouped using an HMM, based on the log-likelihood values of the HMM, to improve the training efficiency. The log-likelihood values of each data samples are calculated using the trained HMM. Then, the data samples of similar likelihood are grouped.

In the second stage 302, an ANN is generated for each of the clusters of data achieved in the first stage 300. For example, if there are three clusters of data, three ANNs are generated where each ANN is associated with an individual cluster. The structure of each ANN is different from the others because the input dataset for each ANN is different. The performance of ANN varies with varying initial weights. To achieve optimal initial weights an EA based GA may be used. The GA may be applied to obtain optimal initial connection weights of each ANN as described in G. Haixiang, L. Xiuwu, Z. Kejun, D. Chang, and G. Yanhui, "Optimizing reservoir features in oil exploration management based on fusion of soft computing", Applied Soft Computing, 11(1) (2011), pp. 1144-1155 incorporated herein by reference in its entirety.

The initial weight for an ANN structure is identified by the GA and then the ANN is trained using a back propagation algorithm as would be understood by one of ordinary skill in the art. The object here is to attain a minimum error formulated using the error function Root Mean Square Error (RMSE) between target and actual outputs averaged over all training examples. The algorithm to achieve an optimal initial weight for an ANN structure is provided in Algorithm 1.

---

Algorithm 1: Obtain an optimal initial connection weights for an ANN structure given the training dataset

---

Input: the training dataset, ANN structure along with the activation function
Output: the set of optimal initial weights: cu
generate initial population;
while EA terminating condition is not satisfied do
　τ = population size/2;
　for count = 1 to τ do
　　select any two parent chromosomes following a
　　uniform distribution; perform cross over between
　　these two chromosomes;
　　use the edited parents as offspring chromosome to create a new
　　population;
　　if fitness values of each of the chromosomes in a population do not
　　converge for a number of iteration
　　then
　　　perform mutation operation by introducing a random perturbation to
　　　any of the cell of randomly selected chromosome;
　　end
　end
for each chromosome do
　initialize the ANN structure using the chromosome
　values as initial weight; train the ANN using training
　dataset and back propagation algorithm; compute
　MSE for the training dataset;
　use the computed MSE as fitness value for the corresponding
　chromosome;
end
for i = 1 to 4 × τ do
　select 20% of 2 × τ chromosomes randomly;
　perform a tournament selection between the $i^{th}$ chromosome's
　fitness value and the that of the selected 20% chromosomes from
　the previous line;

---

Algorithm 1: Obtain an optimal initial connection weights for an ANN structure given the training dataset

--- assign the tournament score obtained to the corresponding
　chromosome;
end
sort the chromosomes in an descending order based on the
respective tournament scores; select the half of the top scorer
chromosomes as next generation solution;
end
cu = the chromosome with the best fitness value in the last generation;

---

Algorithm 1 requires an ANN structure as an input to achieve an optimal initial weight values. To obtain an optimal ANN structure for each of the clustered datasets, an EA was applied where the chromosome represents the number of neurons at a hidden layer of a three layer (i.e., input layer, hidden layer and output layer) ANN. The objective function of the GA is to achieve a minimum value of the prediction error in terms of RMSE. Prior to calculating the RMSE, each ANN represented by an individual chromosome of the GA produces prediction value for a given input data vector. Hence, the ANN is trained before it is used to evaluate using the objective function. To achieve optimal initial weight for each ANN structure created by each individual chromosome the GA described in Algorithm 1 is applied. Hence, two GA's are used as co-evolutionary algorithm where, one GA is executed inside another one. The chromosomes of the first GA generate a number of ANN structures and the second GA provides optimal initial weights for each of the ANN structures. The algorithm to achieve an optimal ANN structure with optimal initial weights is described in Algorithm 2.

---

Algorithm 2: Obtain an optimal ANN structure with optimal initial weights given the training dataset

---

Input: the training dataset
Output: the set of optimal ANN structure with optimal initial weights
generate initial population where each chromosome will represent an
ANN structure;
while EA terminating condition is not satisfied do
　τ = population size/2;
　for count = 1 to τ do
　　select any two parent chromosomes following a uniform
　　distribution; perform cross over between these two
　　chromosomes;
　　use the edited parents as offspring chromosome to create a new
　　population;
　　if fitness values of each of the chromosomes in a population do not
　　converge for a number of iteration
　　then
　　　perform mutation operation by introducing a random perturbation to
　　　any of the cell of randomly selected chromosome;
　　end
　end
　for each chromosome do
　　generate an ANN structure from the chromosome values;
　　obtain the optimal initial weights for the ANN structure generated
　　using Algorithm 1; train the ANN using training dataset and back
　　propagation algorithm;
　　compute MSE for the training dataset using the trained ANN;
　　use the computed MSE as fitness value for the corresponding
　　chromosome;
　end
　for i = 1 to 4 × τ do
　　select 20% of 2 × τ chromosomes randomly;
　　perform a tournament selection between the $i^{th}$ chromosome's fitness
　　value and the that of the selected 20% chromosomes from the
　　previous line; assign the tournament score obtained to the
　　corresponding chromosome;
　end -continued Algorithm 2: Obtain an optimal ANN structure with optimal initial
weights given the training dataset sort the chromosomes in an descending order based on the respective
tournament scores, select the half of the top scorer chromosomes as
next generation solution;
end
The ANN structure with the optimal initial weights represented by the
best chromosome in the last generation;

As described previously herein, genetic algorithms are used for training in two phases. A first GA is used to determine the optimal structure of the ANN and a second GA is used inside the first GA to obtain the optimal weights for each ANN. The RMSE and CC is used as performance measures between the predicted and the actual values.

In stage three 304, permeability is predicted using the hybrid HMIM co-evolutionary ANN model for a new unseen input data vector. When a new predictor vector (one or more formation properties) is fed into the model, log-likelihood score is calculated for the data vector using the HMM. The corresponding group wherein the log-likelihood score fits in is identified. The ANN trained using the dataset from that group is then applied to generate forecast using the new input data vector.

Figure 4:
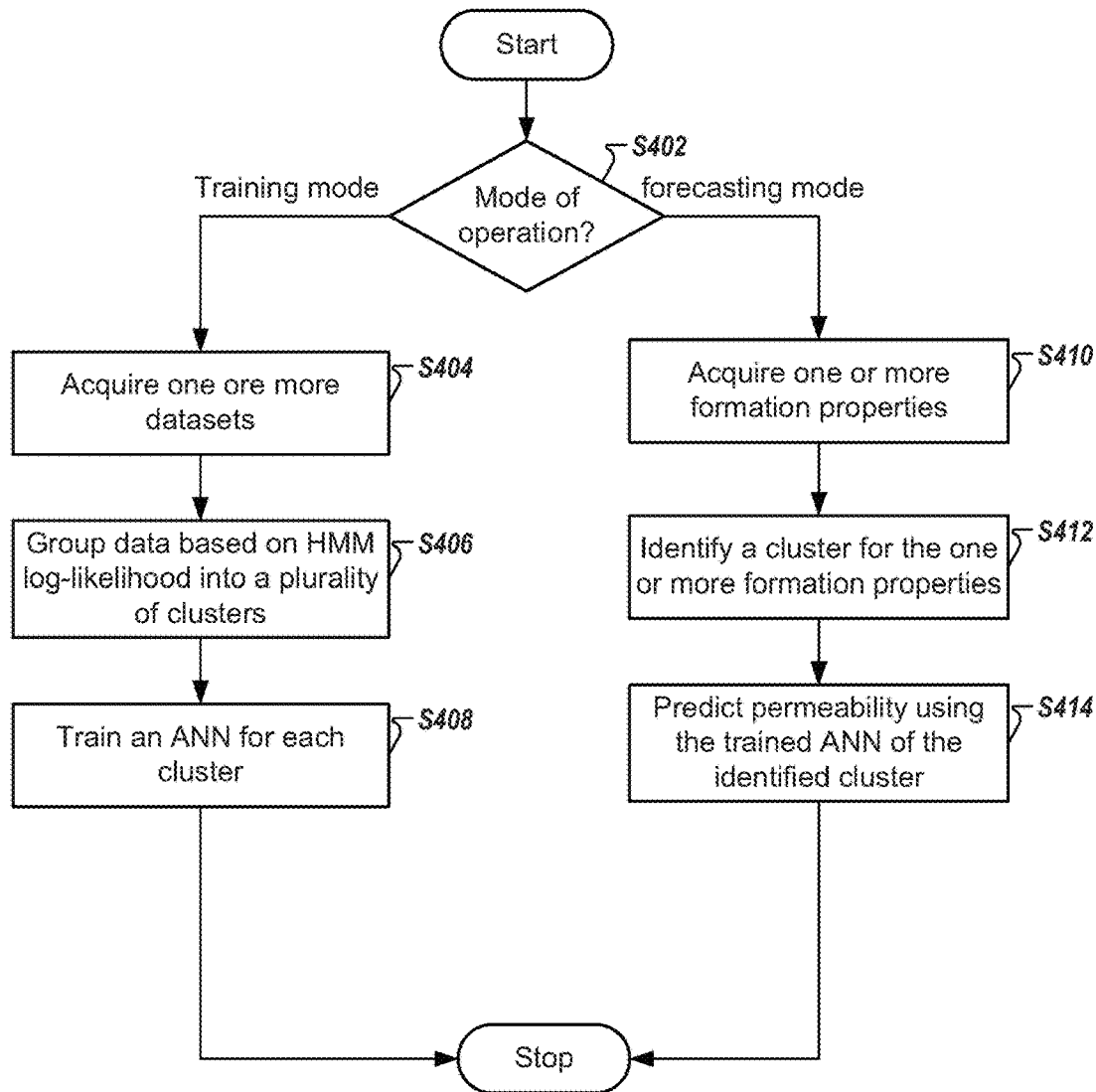
FIG. 4 is a flow chart that shows a method for permeability prediction according to one example.

FIG. 4 is a flow chart for permeability prediction according to one example. At step S402, the server 100 may determine the mode of operation of the system. In response to determining that the mode of operation is "training mode", the flow goes to step S404. In response to determining that the mode of operation is forecasting mode, the flow goes to step S410. The server 100 may detect a user input identifying the mode of operation via the permeability prediction device 104. Alternatively, when the server 100 receives an input from the permeability prediction apparatus 104, the CPU 700 may check to see whether a trained ANN is associated with the permeability prediction apparatus 104. For example, the trained ANN may be associated with a geographical location of the reservoir and/or with a unique identifier of the permeability prediction apparatus 104. In response to determining that a trained ANN is available, the CPU 700 identifies the mode of operation as "forecasting" and the flow goes to step S410. In response to determining that a trained ANN is not available, the CPU 700 identifies the mode of operation as "training" mode and the flow goes to step S404.

At step S404, the server 100 may acquire one or more datasets associated with one or more oil reservoirs or geological formations. Each dataset may include one or more formation properties and a measured permeability. Data in each dataset may be divided for training and testing. For example, 80% of the data may be used for training an ANN and 20% of the data may be used to test the trained ANN. At step S406, the CPU 700 may group the data based on HMM log-likelihood as described previously herein. At step S408, an ANN for each of the groups (clusters), identified at step S406, may be trained using algorithm 1 and algorithm 2 as described previously herein. Trained ANNs (e.g., weights of the ANN structure) are stored in the reservoir information database 106 and/or the memory 702.

At step S410, the CPU 700 may acquire one or more formation properties associated with a geological formation. For example, the one or more formation properties may be received from a permeability prediction apparatus 104. At step S412, the CPU 700 may identify the group to which the one or more formation properties belong using the trained HMM. At step S414, the CPU 700 determines the predicted permeability as a function of the one or more formation properties using the trained ANN associated with the group identified at step S412.

Figure 5:
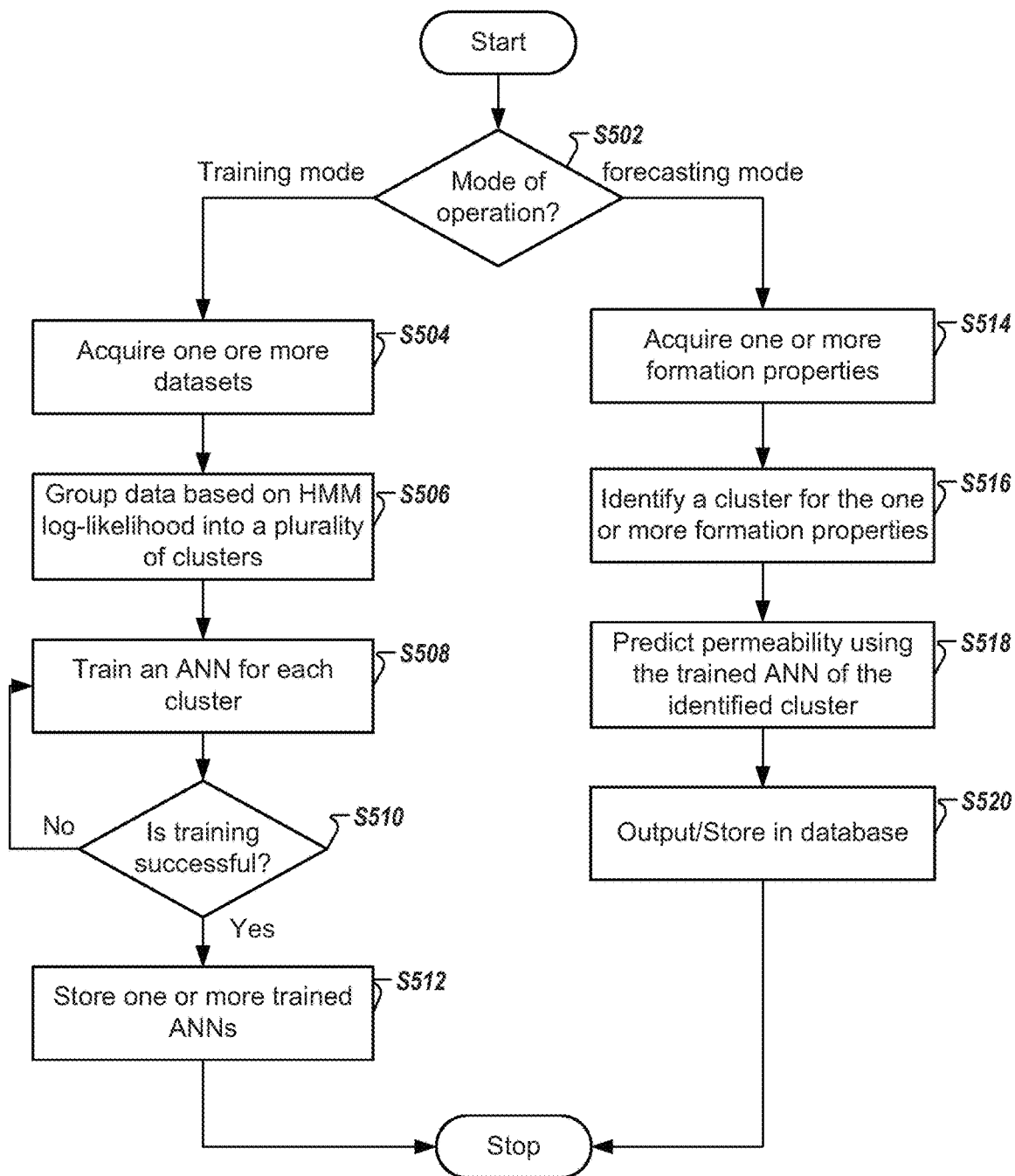
FIG. 5 is a flow chart that shows a method for permeability prediction according to one example.

FIG. 5 is a flow chart for permeability prediction according to one example. At step S502, the server 100 may determine the mode of operation of the system. In response to determining that the mode of operation is "training mode", the flow goes to step S504. In response to determining that the mode of operation is "forecasting", the flow goes to step S514. For example, the server 100 may detect a user input identifying the mode of operation via the permeability prediction device 104. Additionally, based on the reservoir location and/or whether the training has been completed, the CPU 700 may automatically determine the mode of operation.

At step S504, the server 100 may acquire one or more datasets associated with one or more oil reservoirs or geological formations. At step S506, the CPU 700 may group the data based on HMM log-likelihood as described previously herein. At step S508, an ANN for each of the groups identified at step S506 may be trained using algorithm 1 and algorithm 2 as described previously herein. Then, at step S510, the CPU 700 may determine whether the training is successful. In response to determining that the training is successful, the flow goes to step S512. In response to determining that the training is not successful the flow goes back to step S508. For example, the dataset may be divided into a training set and a testing set. Then, a predetermined accuracy threshold may be used to determine whether the training is successful as would be understood by one of ordinary skill in the art. The CPU 700 may compare the predicted permeability with the measured permeability. Then, the CPU 700 may compare an accuracy value (e.g., percentage difference, difference) with the predetermined accuracy threshold to determine whether the training is successful. At step S512, the one or more trained ANNs are stored in the memory 702 and/or the reservoir information database 106.

At step S514, the CPU 700 may acquire one or more formation properties associated with a geological formation. At step S516, the CPU 700 may identify the group to which the one or more formation properties belong. At step S518, the CPU 700 determines the predicted permeability. In one example, the permeability prediction apparatus 104 may connect to the server 100 to download the trained ANN associated with the group identified at step S516.

At step S520, the CPU 700 may output the predicted permeability to a user and/or to other host applications to determine an amount of oil based on the predicted permeability.

To illustrate the capabilities of the system described herein, exemplary results are presented.

To evaluate the system and methodology described herein, "HMM based Co-evolutionary ANN hybrid", datasets collected from exploration wells in the Middle East are used. During drilling operation of these exploration wells, selected carbonate limestone rock sections are cored using special equipment in order to extract intact rock cores that are almost around 30 to 40 feet in length and around 4 to 6 inches in diameter. From these big cores, samples are extracted at different points and permeability is measured. Ten inputs of log values from these well log data are considered as input parameters in developing the models. The system described herein predicts the core permeability expressed in logarithmic scale. Selected inputs affect the permeability of the well-logs. Table 1 provides the statistical descriptions of the predictor variables.

TABLE 1

The input parameters of the dataset and their statistical analysis.

| Input Parameters | Description | Min | Max | Mean | Std. Dev. |
|---|---|---|---|---|---|
| Microspherically focused log (MSFL) | The measure of the boreholes's electrical resistivity | 0.5377 | 2.4368 | 1.1762 | 0.4575 |
| Deep Resistivity (RT) | A measure of the electrical resistivity of the borehole used in the mine | 0.0089 | 10.0000 | 1.3108 | 3.3131 |
| Porosity log (PHIT) | The statistical measurement or ratio of pore volume to the volume of rock | 0.0355 | 0.2909 | 0.1529 | 0.0679 |
| Density log (RHOB) | The measure of bulk density of the formation. | 2.1810 | 2.6682 | 2.4371 | 0.1419 |
| Water Saturation (SWT) | The water saturation is a measurement of porosity, resistivity, and other logs. | 0.0400 | 1.0000 | 0.1703 | 0.1783 |
| Neutron porosity log (NPHI) | The measurement of hydrogen content in a formation. | 0.0300 | 0.2611 | 0.1371 | 0.0517 |
| Caliper log (CALI) | The diameter of the borehole at varying depth | 8.1558 | 8.4891 | 8.4105 | 0.1038 |
| Computed Tomography (CT) | Indicate hydrate and aqueous phase saturations | 0.0001 | 0.1121 | 0.0495 | 0.0305 |
| Density correction log (DRHO) | Records absolute deviations of log signal | 0.0030 | 0.1298 | 0.0.0570 | 0.0277 |
| Gamma Ray (GR) | It is a measurement of the natural radioactivity of the formation along the borehole. | 6.0399. | 31.0351 | 14.7926 | 6.0399 |

To evaluate the performance of the system described herein, HMM-COEA-ANN, 5-fold cross-validations are used. The models that have been compared with the methodology described herein are the simple Co-Evolutionary ANN model (COEA-ANN), K-means cluster based Co-Evolutionary ANN model (Kmeans-COEA-ANN), and Fuzzy C-means cluster based Co-Evolutionary ANN model (FCM-COEA-ANN) with varying number of clusters (e.g. 2, 3 and 4). The methodology described herein is also compared with the existing earlier hybrid models Hybrid-FFS and Hybrid-FSF along with simple Computational Intelligence (CI) models (e.g., Support Vector Regression (SVR), Fuzzy Logic (FL), Functional Network (FN)) described in T. Helmy, A. Fatai, and A. K. Faisal, "Prediction of porosity and permeability of oil and gas reservoirs using hybrid computational intelligence models", Expert Systems with Applications, 7(37) (2010), pp. 5353-5363.

Figure 6:
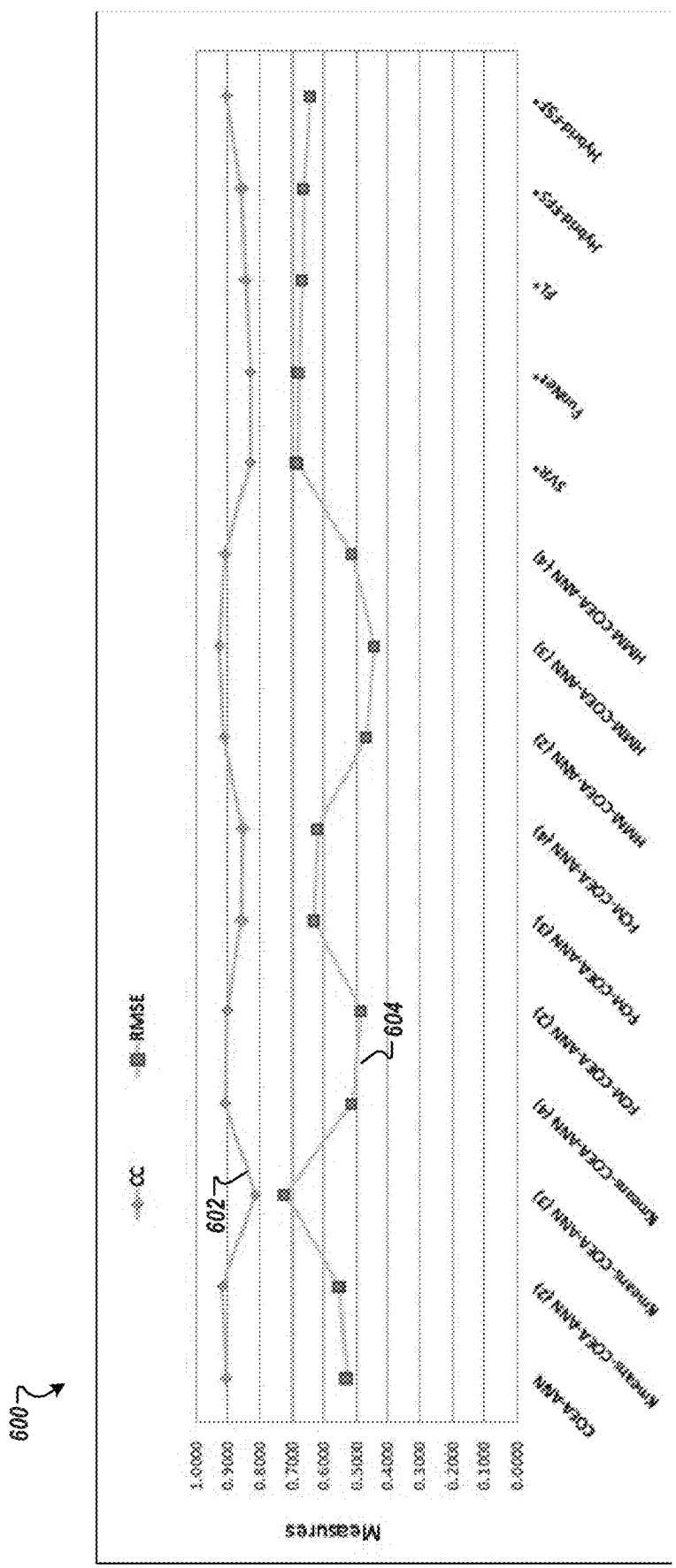
FIG. 6 is a graph that shows the results of comparison of a plurality of permeability prediction methods according to one example.

FIG. 6 is a graph 600 that shows the results of comparing a plurality of permeability prediction methods according to one example. The graph 600 shows the permeability prediction accuracies of the method described herein among other methods. The performance measures used are RMSE (Trace 604) and CC (Trace 602). Graph 600 clearly depict that the performance of non-hybrid model e.g. SVR, FunNet, FL are insignificant comparing to the hybrid models. The methodology described herein based on a hybrid model of HMM-COEA-ANN for three clusters achieved the best performance (the least RMSE and highest CC) compared to the other models. The performances of few hybrid approaches with K-means and Fuzzy C-means algorithm to cluster the dataset following the COEA-ANN model does not improve the permeability prediction performance compared to simple COEA-ANN model. Therefore, clustering may not always improve accuracy. Each cluster of data through the methodology described herein HMM based model represents the problem better than that of K-means and Fuzzy C-means and so EA based ANN performed best on the HMM based clustered data. Furthermore, the Hybrid-FFS and Hybrid-FSF are also showing lower accuracy in terms of RMSE and CC than the methodology described herein as shown in Table 2.

TABLE 2

Performance of the proposed model HMM-COEA-ANN and other models

| Model | CC | RMSE |
|---|---|---|
| COEA-ANN | 0.9040 | 0.5293 |
| Kmeans-COEA-ANN (2) | 0.9147 | 0.5496 |
| Kmeans-COEA-ANN (3) | 0.8156 | 0.7219 |
| Kmeans-COEA-ANN (4) | 0.9067 | 0.5126 |
| FCM-COEA-ANN (2) | 0.9010 | 0.4827 |
| FCM-COEA-ANN (3) | 0.8592 | 0.6296 |
| FCM-COEA-ANN (4) | 0.8546 | 0.6213 |
| HMM-COEA-ANN (2) | 0.9112 | 0.4692 |
| HMM-COEA-ANN (3) | 0.9248 | 0.4403 |
| HMM-COEA-ANN (4) | 0.9067 | 0.5126 |
| SVR* | 0.8328 | 0.6845 |
| FunNet* | 0.8332 | 0.6811 |
| FL* | 0.8450 | 0.6695 |
| Hybrid-FFS* | 0.8586 | 0.6658 |
| Hybrid-FSF* | 0.9019 | 0.6429 |

Next, a hardware description of the server 100 according to exemplary embodiments is described with reference to FIG. 7. In FIG. 7, the server 100 includes a CPU 700 which performs the processes described herein. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the server 100 communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

In order to achieve the server 100, the hardware elements may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The server 100 in FIG. 7 also includes a network controller 706, such as an Intel Ethernet PRO network interface card from Intel Corporation of America, for interfacing with network 102. As can be appreciated, the network 102 can be a public network, such as the Internet, or a private network such as LAN or WAN network, or any combination thereof and can also include PSTN or ISDN sub-networks. The network 102 can also be wired, such as an Ethernet network, or can be wireless such as a cellular network including EDGE, 3G and 4G wireless cellular systems. The wireless network can also be WiFi, Bluetooth, or any other wireless form of communication that is known.

The server 100 further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as an optional touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the server 100, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the server 100. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein.

Figure 8:
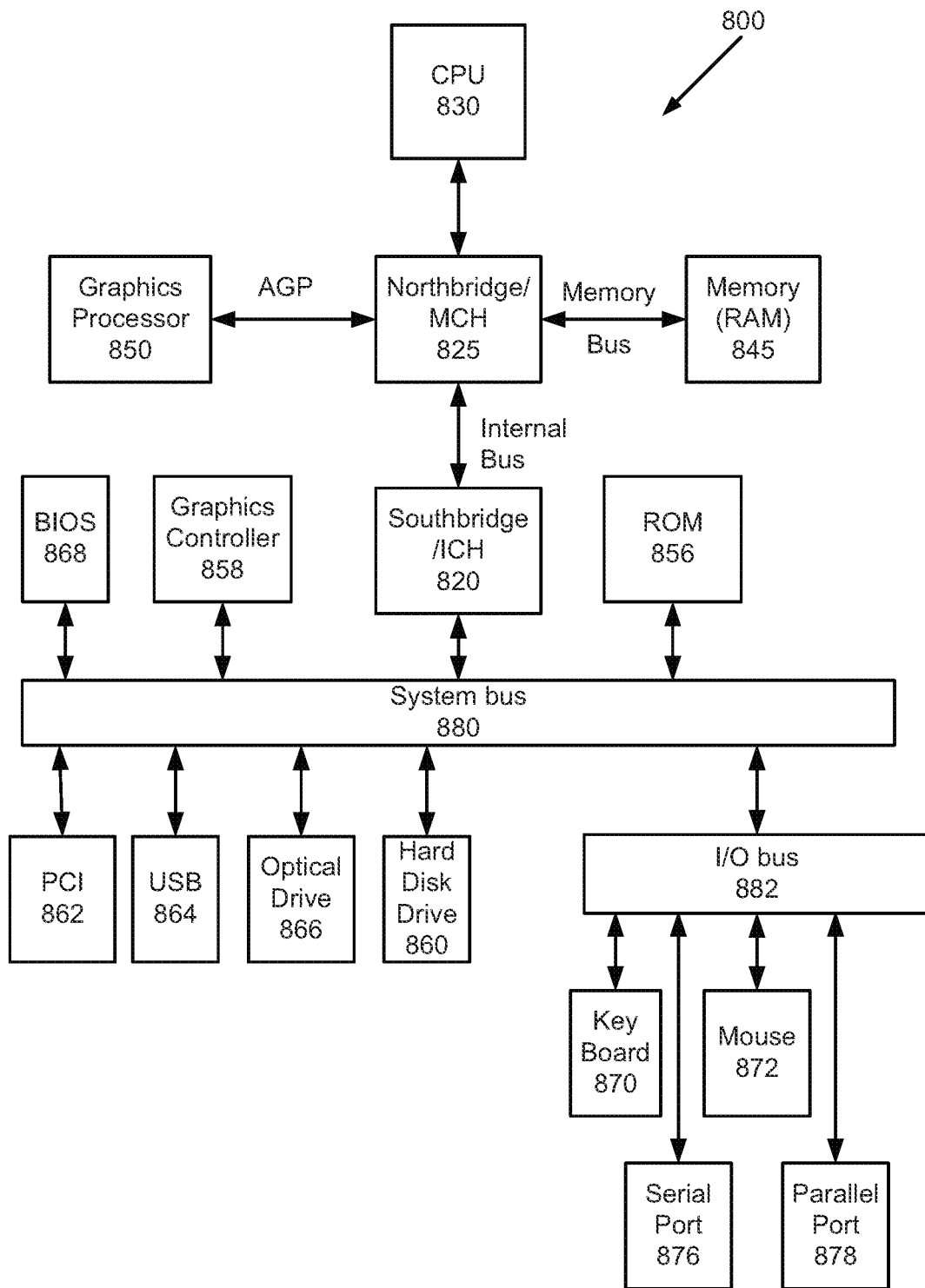
FIG. 8 is an exemplary block diagram of a data processing system according to one example.

FIG. 8 shows a schematic diagram of a data processing system, according to certain embodiments, for predicting permeability of a reservoir utilizing the methodologies described herein. The data processing system is an example of a computer in which specific code or instructions implementing the processes of the illustrative embodiments may be located to create a particular machine for implementing the above-noted process.

Figure 9:
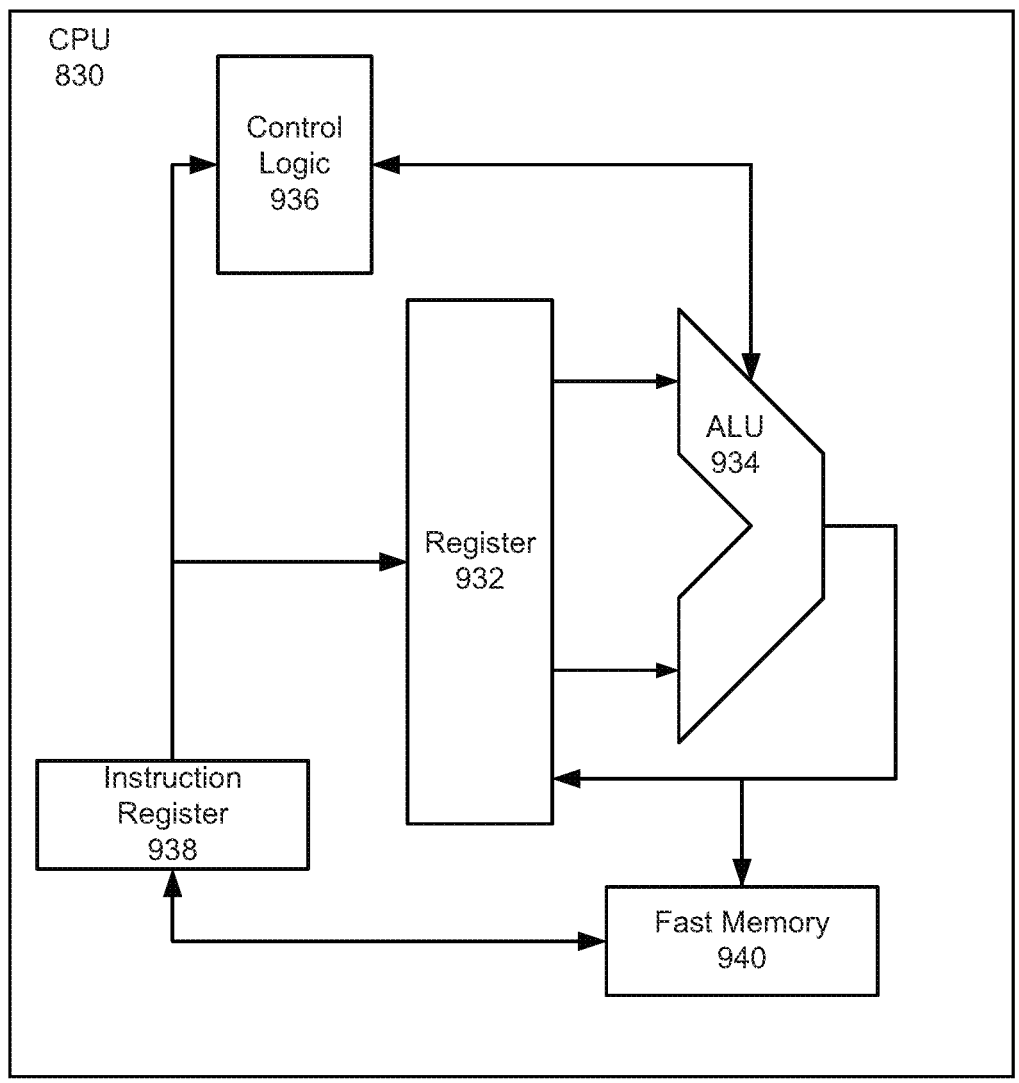
FIG. 9 is an exemplary block diagram of a central processing unit according to one example.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU 830 may contain one or more processors and may even be implemented using one or more heterogeneous processor systems. For example, FIG. 9 shows one implementation of CPU 830.

Further, in the data processing system 800 of FIG. 8, SB/ICH 820 is coupled through a system bus 880 to an I/O Bus 882, a read only memory (ROM) 856, an universal serial bus (USB) port 864, a flash binary input/output system (BIOS) 868, and a graphics controller 858. In one implementation, the I/O bus can include a super I/O (SIO) device.

PCI/PCIe devices can also be coupled to SB/ICH 820 through a PCI bus 862. The PCI devices may include, for example, Ethernet adapters, add-in cards, and PC cards for notebook computers. Further, the hard disk drive (HDD) 860 and optical drive 866 can also be coupled to the SB/ICH 820 through the system bus 880. The Hard disk drive 860 and the optical drive or CD-ROM 866 can use, for example, an integrated drive electronics (IDE) or serial advanced technology attachment (SATA) interface.

In one implementation, a keyboard 870, a mouse 872, a serial port 876, and a parallel port 878 can be connected to the system bus 880 through the I/O bus 882. Other peripherals and devices that can be connected to the SB/ICH 820 include a mass storage controller such as SATA or PATA (Parallel Advanced Technology Attachment), an Ethernet port, an ISA bus, a LPC bridge, SMBus, a DMA controller, and an Audio Codec (not shown).

In one implementation of CPU 830, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation, the instructions are decoded according to a hardwired method, and in another implementation, the instructions are decoded according a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

The present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

The functions and features described herein may also be executed by various distributed components of a system. For example, one or more processors may execute these system functions, wherein the processors are distributed across multiple components communicating in a network. The distributed components may include one or more client and server machines, which may share processing in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

The hardware description above, exemplified by any one of the structure examples shown in FIG. 7 or 8, constitutes or includes specialized corresponding structure that is programmed or configured to perform the algorithms shown in FIGS. 4 and 5.

A system which includes the features in the foregoing description provides numerous advantages to users. In particular, the system determines an estimate of the permeability of a reservoir. In addition, the methodology described herein may be used to determine other properties such as porosity of an oil reservoir.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for predicting permeability, the method comprising:
    receiving an input from a permeability prediction apparatus;
    determining whether a trained artificial neural network is associated with a unique identifier of the permeability prediction apparatus and a geographical location of one or more geological formations;
    setting an operation mode as a training mode in response to determining that the trained artificial neural network is not associated with the unique identifier of the permeability prediction apparatus and the geographical location of the one or more geological formations;
    setting the operation mode as a forecasting mode in response to determining that the trained artificial neural network is associated with the unique identifier of the permeability prediction apparatus and the geographical location of the one or more geological formations;
    acquiring, using processing circuitry, data associated with the one or more geological formations when the mode of operation is training mode;
    calculating, using the processing circuitry and a trained Hidden Markov model, log-likelihood values to group the data into a plurality of clusters when the mode of operation is training mode;
    training, using the processing circuitry, an artificial neural network for each of the plurality of clusters using a co-evolutionary genetic algorithm having at least two genetic algorithms when the mode of operation is training mode, wherein a second genetic algorithm is executed inside a first genetic algorithm, the first genetic algorithm generating a number of artificial neural network structures associated with each cluster of the plurality of clusters, each of the artificial neural network structure having initial weights determined by the second genetic algorithm, the first genetic algorithm including identifying 20% of the chromosomes in a random manner;
    determining whether the training is successful based on a predetermined accuracy threshold;
    storing the weights of the artificial neural network structure in a reservoir information database when the training is successful;
    acquiring, using communication circuitry, one or more formation properties corresponding to a geological formation when the mode of operation is forecasting mode, the one or more formation properties includes a micro-spherically focused log, deep resistivity, a porosity log, a density log, water saturation, a neutron porosity log, a caliper log, computed tomography, a density correction log, and gamma ray;
    determining, using the processing circuitry and the trained Hidden Markov model, a log-likelihood score associated with the one or more formation properties when the mode of operation is forecasting mode;
    identifying, using the processing circuitry, a cluster associated with the one or more formation properties as a function of the log-likelihood score when the mode of operation is forecasting mode;
    predicting, using the processing circuitry, a permeability based at least in part on the one or more formation properties and the trained artificial neural network associated with the identified cluster when the mode of operation is forecasting mode; and
    determining an amount of oil based on the predicted permeability.

2. The method of claim 1, further comprising:
    serving the permeability to one or more host applications to determine a productivity estimate of the geological formation.

3. The method of claim 1, wherein the mode of operation is determined based on a location of the geological formation.

4. The method of claim 1, further comprising:
generating an initial population;
updating a population based on a cross over between two chromosomes selected using a uniform distribution;
repeating the updating step until a first condition is satisfied;
initializing an artificial neural network structure for each chromosome using the chromosome value as an initial weight;
training the artificial neural network structure using the data and a back propagation algorithm;
performing a tournament selection for the identified chromosome; and
selecting the chromosome with a best fitness value as an initial weight.

5. A system for permeability prediction, the system comprising:
one or more permeability prediction apparatuses;
one or more logging tools associated with each of the permeability prediction apparatuses; and
a server associated with the one or more permeability prediction apparatus including
communication circuitry configured to
receive an input from a permeability prediction apparatus,
acquire data associated with one or more geological formations when operating in a training mode, and
acquire one or more formation properties from a logging tool associated with the permeability prediction apparatus corresponding to a geological formation when a mode of operation is forecasting mode, the one or more formation properties includes a microspherically focused log, deep resistivity, a porosity log, a density log, water saturation, a neutron porosity log, a caliper log, computed tomography, a density correction log, and gamma ray; and
processing circuitry configured to
determine whether a trained artificial neural network is associated with a unique identifier of the permeability prediction apparatus and a geographical location of one or more geological formations,
set an operation mode as the training mode in response to determining that the trained artificial neural network is not associated with the unique identifier of the permeability prediction apparatus and the geographical location of the one or more geological formations,
set the operation mode as the forecasting mode in response to determining that the trained artificial neural network is associated with the unique identifier of the permeability prediction apparatus and the geographical location of the one or more geological formations,
calculate, using a trained Hidden Markov model, log-likelihood values to group the data into a plurality of clusters when the mode of operation is training mode,
train an artificial neural network for each of the plurality of clusters using a co-evolutionary genetic algorithm having at least two genetic algorithms when the mode of operation is training mode, wherein a second genetic algorithm is executed inside a first genetic algorithm, the first genetic algorithm generating a number of artificial neural network structures associated with each cluster of the plurality of clusters, each of the artificial neural network structure having initial weights determined by the second genetic algorithm, the first genetic algorithm including identifying 20% of the chromosomes in a random manner,
determine whether the training is successful based on a predetermined accuracy threshold,
store the weights of the artificial neural network structure in a reservoir information database when the training is successful,
determine, using the trained Hidden Markov model, a log-likelihood score associated with the one or more formation properties when the mode of operation is forecasting mode,
identify a cluster associated with the one or more formation properties as a function of the log-likelihood score when the mode of operation is forecasting mode,
predict a permeability based at least in part on the one or more formation properties and a trained artificial neural network associated with the identified cluster when the mode of operation is forecasting mode, and
determine an amount of oil based on the predicted permeability.

6. The system of claim 5, wherein the processing circuitry is further configured to:
serve the permeability to one or more host applications to determine a productivity estimate of the geological formation.

7. The system of claim 5, wherein the mode of operation is determined based on a location of the geological formation.

8. A non-transitory computer readable medium storing computer-readable instructions therein which when executed by a computer cause the computer to perform a method for predicting permeability, the method comprising:
receiving an input from a permeability prediction apparatus;
determining whether a trained artificial neural network is associated with a unique identifier of the permeability prediction apparatus and a geographical location of one or more geological formations;
setting an operation mode as a training mode in response to determining that the trained artificial neural network is not associated with the unique identifier of the permeability prediction apparatus and the geographical location of the one or more geological formations;
setting the operation mode as a forecasting mode in response to determining that the trained artificial neural network is associated with the unique identifier of the permeability prediction apparatus and the geographical location of the one or more geological formations;
acquiring data associated with one or more geological formations when the mode of operation is training mode;
calculating, using a trained Hidden Markov model, log-likelihood values to group the data into a plurality of clusters when the mode of operation is training mode;
training an artificial neural network for each of the plurality of clusters using a co-evolutionary genetic algorithm having at least two genetic algorithms when the mode of operation is training mode wherein a second genetic algorithm is executed inside a first genetic algorithm, the first genetic algorithm generating a number of artificial neural network structures associated with each cluster of the plurality of clusters, each of the artificial neural network structure having initial weights determined by the second genetic algorithm, the first genetic algorithm including identifying 20% of the chromosomes in a random manner;

determining whether the training is successful based on a predetermined accuracy threshold;

storing the weights of the artificial neural network structure in a reservoir information database when the training is successful;

acquiring one or more formation properties corresponding to a geological formation when the mode of operation is forecasting mode, the one or more formation properties includes a micro-spherically focused log, deep resistivity, a porosity log, a density log, water saturation, a neutron porosity log, a caliper log, computed tomography, a density correction log, and gamma ray;

determining, using the trained Hidden Markov model, a log-likelihood score associated with the one or more formation properties when the mode of operation is forecasting mode;

identifying a cluster associated with the one or more formation properties as a function of the log-likelihood score when the mode of operation is forecasting mode;

predicting a permeability based at least in part on the one or more formation properties and the trained artificial neural network associated with the identified cluster when the mode of operation is forecasting mode; and determining an amount of oil based on the predicted permeability.

* * * * *